United States Patent
Ghalili et al.

(10) Patent No.: US 11,229,610 B2
(45) Date of Patent: *Jan. 25, 2022

(54) CANNABINOID AND MENTHOL GEL COMPOSITIONS, PATCHES AND METHODS

(71) Applicants: Babak Ghalili, New York, NY (US); Emma Ghalili, New York, NY (US)

(72) Inventors: Babak Ghalili, New York, NY (US); Emma Ghalili, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/807,229

(22) Filed: Mar. 3, 2020

(65) Prior Publication Data

US 2020/0315986 A1    Oct. 8, 2020

Related U.S. Application Data

(63) Continuation-in-part of application No. 16/558,780, filed on Sep. 3, 2019, which is a continuation-in-part of application No. 16/419,336, filed on May 22, 2019, now Pat. No. 10,751,299.

(60) Provisional application No. 62/726,713, filed on Sep. 4, 2018.

(51) Int. Cl.

| | |
|---|---|
| A61K 9/70 | (2006.01) |
| A61K 31/352 | (2006.01) |
| A61K 36/185 | (2006.01) |
| A61K 47/36 | (2006.01) |
| A61K 47/14 | (2017.01) |
| A61K 47/12 | (2006.01) |
| A61K 47/10 | (2017.01) |
| A61K 9/06 | (2006.01) |

(52) U.S. Cl.
CPC .......... *A61K 9/7023* (2013.01); *A61K 31/352* (2013.01); *A61K 36/185* (2013.01); *A61K 47/10* (2013.01); *A61K 47/12* (2013.01); *A61K 47/14* (2013.01); *A61K 47/36* (2013.01); *A61K 9/06* (2013.01)

(58) Field of Classification Search
CPC .. A61K 9/7023; A61K 31/352; A61K 36/185; A61K 47/36; A61K 47/12; A61K 47/10
See application file for complete search history.

(56) References Cited

U.S. PATENT DOCUMENTS

| | | | |
|---|---|---|---|
| 5,869,087 A | 2/1999 | Hirano et al. | |
| 9,839,693 B2 * | 12/2017 | Borja | A61K 39/3955 |
| 10,813,889 B2 * | 10/2020 | Ghalili | A61P 25/00 |
| 2005/0281881 A1 | 12/2005 | Woeller et al. | |
| 2011/0207817 A1 | 8/2011 | Wetterer et al. | |
| 2016/0184212 A1 * | 6/2016 | Casasanta, III | A61N 5/0616 604/20 |
| 2017/0020942 A1 | 1/2017 | Naheed | |
| 2018/0000698 A1 * | 1/2018 | Kakinuki | A61K 8/8158 |
| 2018/0344860 A1 * | 12/2018 | Naheed | A61K 36/185 |
| 2019/0110981 A1 | 4/2019 | Weimann | |
| 2019/0247299 A1 * | 8/2019 | Cameron | A61K 36/28 |
| 2020/0108025 A1 * | 4/2020 | Ghalili | A61K 9/06 |

FOREIGN PATENT DOCUMENTS

| | | | |
|---|---|---|---|
| AU | 2017239512 | * | 4/2019 |
| CN | 104997644 | * | 10/2015 |
| RU | 2102978 C1 | | 1/1998 |
| WO | 2017059088 A1 | | 4/2017 |

OTHER PUBLICATIONS

Abualhasan, Murad, et al. "GC Mehtod and Validation for the Analysis of Menthol in Suppository Pharmaceutical Dosage Form," Internnational Journal of Analytical Chemistry, vol. 2017, Mar. 6, 2017, 4 pages.
Echo, "What is Full-Spectrum Hemp Oil and Why is it Important" Downloaded Apr. 24, 2020, Date May 5, 2017, 5 Pages.
Nagarkatti, Prakesh et al. "Cannabinoids as novel anti-inflammatory drugs." Future medicinal chemistry vol. 1,1 (2009), 25 Pages.
Notification of Transmittal of The International Search Report and the Written Opinion of The International Searching Authority, or The Declaration, Application No. PCT/US19/49294, dated Jan. 21, 2020, 21 Pages.
Notification of transmittal of The International Search Report and The Written Opinion of The International Searching Authority, or The Declaration, Application No. PCT/US20/20722, dated Jun. 10, 2020, 16 Pages.
Sapirstein, Alliqua CEO: Hydrogel-Based Transdermal Drug Delivery, an Innovative Alternative, Drug Discovery and Development, Sep. 19, 2013. 3 Pages.
Schimmel, "What is Denatured Alcohol?" Feb. 5, 2013. 1 Page.

(Continued)

*Primary Examiner* — Mina Haghighatian
(74) *Attorney, Agent, or Firm* — Ziegler IP Law Group, LLC (57) ABSTRACT

The present disclosure relates to compositions methods of use and methods of manufacturing, hydrous hydrogel compositions useful as topical oral analgesics including cannabinoids and menthol where the menthol component can be a stabilized menthol composition comprising menthol and at least one menthol stabilizer compound including undecylenic acid methyl ester, undecylenic acid or a salt of undecylenic acid.

20 Claims, 6 Drawing Sheets

(56) References Cited

OTHER PUBLICATIONS

'Systemic Diseases Versus Localized Diseases' Revere Health, Aug. 29, 2016, retrieved from the Internet on May 21, 2020 at <https://reverehealth.com/live-better/systemic-diseases-versus-localized-diseases/> 4 Pages.
Wikipedia, "Carrageenan" 1965, (Retrieved from the Internet on May 18, 2020) at <https://en.wikipedia.org/wiki/Carrageenan> 8 Pages.
Wikipedia, "Menthol" 2013 (Retrieved from the Internet May 18, 2020) at <https://en.wikipedia.org/wiki/Menthol> 12 Pages.
Krizek et al, "Menthol-based hydrophobic deep eutectic solvents: Towards greener and efficient extraction of phytocannabinoids", Journal of Cleaner Production, 193 (2018) 391-396, 6 pages.
Al-Akayleh, "Therapeutic deep eutectic system for capric acid and menthol:Characterization and pharmaceutical application", Journal of Drug Delivery Science and Technology 53 (2019) 1-10, 10 pages.
Muzenda "Interactions of Polar and Nonpolar volatile organic compounds with methyl Ester solvents" 3rd International Conference on Medical Sciences and Chemical Engineering (ICMSCE'2013) Dec. 25-26, 2013 Bangkok (Thailand), 22-26, 5 pages.

\* cited by examiner

CANNABINOID AND MENTHOL GEL COMPOSITIONS, PATCHES AND METHODS

CROSS-REFERENCE TO RELATED APPLICATIONS

This application is a continuation-in-part of U.S. patent application Ser. No. 16/558,780 filed Sep. 3, 2019 which claims priority to and the benefit of U.S. Provisional Patent Application Ser. No. 62/726,713 filed Sep. 4, 2018 and U.S. patent application Ser. No. 16/419,336 filed May 22, 2019, the disclosures of which is incorporated herein by reference in its entirety.

FIELD

The aspects of the present disclosure relate to gel compositions including active agents such as cannabinoids and menthol.

BACKGROUND

There is a need for novel treatments for pain and inflammation on various parts of the body. Some current agents may be ineffective and can, for example, come with unacceptable side effects. Furthermore, there is a growing concern about the overuse of opioid pain treatments.

Hydrogels can be used as a vehicle for the delivery of drugs and other therapeutically active agents. They refer to a network of hydrophilic polymer chains that are generally found as a colloidal gel in which water is the dispersion medium. Hydrogels are highly absorbent (they can contain over 99.9% water) natural or synthetic polymers and can also possess a degree of flexibility very similar to natural tissue, due to their significant water content ("Terminology of polymers and polymerization processes in dispersed systems (IUPAC Recommendations 2011)". Pure and Applied Chemistry 83 (12): 2229-2259. 2011).

BRIEF DESCRIPTION OF THE DRAWINGS

The accompanying drawings illustrate presently preferred embodiments of the present disclosure, and together with the general description given above and the detailed description given below, serve to explain the principles of the present disclosure.

SUMMARY

These and other aspects and advantages of the exemplary embodiments will become apparent from the detailed description. Additional aspects and advantages of the present disclosure will be set forth in the description that follows, and in part will be obvious from the description, or may be learned by practice of the present disclosure. Moreover, the aspects and advantages of the present disclosure may be realized and obtained by means of the instrumentalities and combinations particularly pointed out in the appended claims.

In one embodiment, a transdermal analgesic hydrogel device is provided. The transdermal analgesic hydrogel device includes a surface to be applied to the skin of a mammal, the surface having an area ranging in size from about 9 $cm^2$ to about 256 $cm^2$; water in an amount of from about 70 wt % to about 95 wt %; a biocompatible polymer in an amount of from about 0.5 wt % to about 5 wt %; a polyalcohol in an amount of from about 1 wt % to about 5 wt %; at least one cannabinoid is in an amount of from about 0.1 wt % to about 10 wt %; and menthol is in an amount of from about 1 wt % to about 10 wt %, wherein the menthol is included in a stabilized menthol composition comprising menthol and at least one menthol stabilizer compound including undecylenic acid methyl ester, undecylenic acid or a salt of undecylenic acid.

In another embodiment, a transdermal analgesic hydrogel patch for topical application to the skin of a mammal is provided. The transdermal analgesic hydrogel patch includes water in an amount of from about 70 wt % to about 95 wt %; carageenan in an amount of from about 0.5 wt % to about 5 wt %; glycerin in an amount of from about 1 wt % to about 5 wt %; full spectrum hemp oil in an amount of from about 0.1 wt % to about 10 wt %; and menthol in an amount of from about 1 wt % to about 10 wt %, wherein the menthol is included in a stabilized menthol composition comprising menthol and at least one menthol stabilizer compound including undecylenic acid methyl ester, undecylenic acid or a salt of undecylenic acid.

In another embodiment, a method of treating pain or inflammation in a body part or portion thereof of a mammal using a transdermal hydrogel patch is provided. The transdermal hydrogel patch including a unit dose formulation including water in an amount of from about 70 wt % to about 95 wt %; carageenan in an amount of from about 0.5 wt % to about 5 wt %; glycerin in an amount of from about 1 wt % to about 5 wt %; full spectrum hemp oil in a unit dose amount of from about 2 mg. to about 195 mg; and menthol in a unit dose amount of from about 2 mg. to about 400 mg, wherein the menthol is included in a stabilized menthol composition comprising menthol and at least one menthol stabilizer compound including undecylenic acid methyl ester, undecylenic acid or a salt of undecylenic acid. The method includes administering the transdermal hydrogel patch to a body part of the mammal.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by embodiments of the present disclosure. As used herein, "about" may be understood by persons of ordinary skill in the art and can vary to some extent depending upon the context in which it is used. If there are uses of the term which are not clear to persons of ordinary skill in the art, given the context in which it is used, "about" may mean up to plus or minus 10% of the particular term.

The terms "%", "% by weight", "weight %" and "wt %" are all intended to mean unless otherwise stated, percents by weight based upon a total weight of 100% end composition weight. Thus 10% by weight means that the component constitutes 10 wt. parts out of every 100 wt. parts of total composition.

The term "pharmaceutically acceptable" means that which is useful in preparing a pharmaceutical composition that is generally non-toxic and is not biologically undesirable and includes that which is acceptable for veterinary use and/or human pharmaceutical use.

The term "topically acceptable" means the compound, substance or device may be administered to or onto the surface of a patient, including the skin or other accessible tissues, without substantial harmful effects to the body part and/or its surfaces.

The aspects of the present disclosure relate to compositions including hydrous hydrogel compositions and hydrous hydrogel composition patches for the delivery of an active agent(s). The aspects of the present disclosure also relate to processes for the preparation of, intermediates used in the preparation of, compositions (e.g., pharmaceutical, medical device cosmetic, industrial) containing and the uses of such hydrous hydrogels in the treatment of disorders or application of specified agents to a skin surface.

One specific embodiment of the present disclosure relates to compositions comprising an active agent (including acceptable salt thereof) pharmaceutical composition. Accordingly, in one embodiment, the present disclosure relates to a pharmaceutical composition comprising an active agent, a pharmaceutically acceptable carrier and, optionally, additional medicinal or pharmaceutical agent(s).

Active agents include pharmaceutical agents such as analgesics, decongestants, bronchodilators and other antiasthmatic agents, cardiovascular agents such as beta-blockers, ACE inhibitors, diuretics, antithrombics, etc., diabetic agents, antihistamines, anesthetics, antifungals, antinauseants, antiemetics, antibacterial agents, antifungal agents, corticosteroids, neurological agents, anti-inflammatories, vaccines, biological agents (such as Humera, Enbrel and Remicade), wound healing agents and anticonvulsants. Vitamins (particularly A, C, D and E) are a particular embodiment of an active agent. The concentration of the active ingredient in the gel base is, of course, dependent on the identity of the active agent, the condition and patient being treated and the potency desired.

The formulations of the present disclosure are also useful in the fields of human medicine for the administration of active agents to people (i.e., human patients) and veterinary medicine for the administration of active agents to pets and farm animals.

The aspects of the present disclosure relate to compositions used to relieve pain (i.e., analgesics) and/or inflammation, methods of making such compositions and methods of using such compositions including topically applied (e.g., to skin or another body part) compositions including pharmaceutical compositions, including analgesic and/or anti-inflammatory pharmaceutical compositions for the treatment of pain and/or inflammation, that contain a pharmaceutically effective amount of a pharmaceutically acceptable and effective cannabinoid, menthol and a pharmaceutically acceptable carrier, such as for example, a hydrous hydrogel material, vehicle or carrier. Such compositions may also include, for example, analgesic and/or anti-inflammatory pharmaceutical compositions for the treatment of pain and/or inflammation that contain a pharmaceutically effective amount of a pharmaceutically acceptable and effective cannabinoid, menthol and a pharmaceutically acceptable carrier, such as for example, a hydrous hydrogel material, material or carrier.

The combination of cannabinoid and menthol into a single therapeutic composition, for example, a hydrous hydrogel vehicle, can provide improved and better focused delivery of the actives to a patient than separately applying the cannabinoid and menthol separately (to different areas of the body or layered one on top of another) without the hydrous hydrogel vehicle.

Pharmaceutical compositions, such as, for example, embodiments of the present disclosure, include products and compositions, for example, hydrous hydrogel products and compositions (e.g., patches including hydrous gel patches and hydrous hydrogel patches) including products of a mass of hydrogel composition in a desired size, shape and weight which, in the ordinary course of usage, can be placed topically on a body part (e.g., arm, leg, knee, torso, head, neck, foot as well as those parts that make-up them) for purposes of local and/or systemic administration of particular therapeutic agents for a time sufficient to be effective for purposes of therapeutic activity to the body part and tissues thereof or other tissues remote from the application site in order to provide relief from the malady being suffered (e.g., pain relief though an analgesic and/or anesthetic effect) including a malady of the body part (e.g., pain and/or inflammation) to which the products and compositions of the present disclosure can be directly applied for relief. After being present in contact with the body part for a time sufficient to be effective for purposes of therapeutic activity, they can be removed from the body part. Such application to the body part includes placing the pharmaceutical composition in contact with the skin covering the body part.

Figure 1:
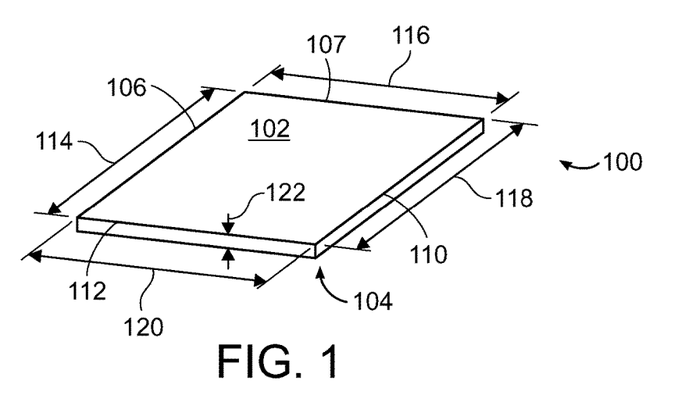
FIG. 1 is a perspective view of an embodiment of the present disclosure.

Embodiments of the present disclosure may be delivered for local or systemic administration to a body part of a person to be treated with the embodiment, for example, a body or skin surface thereof by placing an embodiment of the present disclosure on a body part or skin surface thereof, for example, a knee. leg, back of hand, arm. lower back, upper back, shoulder and forehead, in active agent-transmitting relation thereto, the active agents being cannabinoid, for example, a phytocannabinoid or full spectrum hemp oil, and menthol. Alternatively, an embodiment of the present disclosure may be incorporated into a delivery system, such as a unit dose delivery system or device (e.g. a "patch.""). The delivery system, device or "patch" can be of a suitable size and shape to fit against a body part so as to be applied to the skin surface thereof. A suitable size, for example, is illustrated in FIG. 1 which can include the shape of a square or rectangle 100 or other polygon shape (including, e.g., triangle, pentagon, hexagon, etc.) with surface areas 102 and 104 (on opposing sides) and the dimensions of sides 106, 107, 110 and 112, each ranging in length 114, 116, 118 and 120, respectively ranging from about 3 cm to about 16 cm including each surface area ranging from about 9 $cm^2$ to about 256 $cm^2$, about 4.2 cm to about 6.5 cm including each surface area ranging from about 18 $cm^2$ to about 42 $cm^2$, about 10 cm to about 14 cm including each surface area ranging from about 100 $cm^2$ to about 196 $cm^2$ and about 12 cm to about 16 cm including each surface area ranging from about 144 $cm^2$ to about 256 $cm^2$. For example, embodiments could include patches with sides 106, 107, 110 and 112, each ranging in length 114, 116, 118 and 120, respectively, that are about 6.5 cm.xabout 4.2 cm (surface area about 27.3 $cm^2$), about 10 cm×about 14 cm (surface area about 140 $cm^2$) and about 12 cm×about 16 cm (surface area about 192 $cm^2$).

Thickness 122 can range from about 0.05 cm to about 0.5 cm, about 0.05 cm to about 0.1 cm, about 0.05 cm to about 0.07 cm, about 0.0508 to about 0.06604 cm. Volumes of the patches can range from about 0.45 ml to about 128 ml, about 0.45 ml to about 25.6 ml, about 0.45 ml to about 18 ml, about 0.4572 ml. to about 17 ml, in keeping with the above patch dimensions. For example, the above referenced embodiments that include patches with a surface area 27.3 $cm^2$ based on the above ranges of thickness could have volumes ranging from about 1.4 ml to about 13.7 ml, about 1.4 ml to about 2.73 ml, 1.4 ml to about 1.9 ml, about 1.386 ml to about 1.803 ml; a surface area 140 $cm^2$ based on the above ranges of thickness could have volumes ranging from about 7 ml to about 70 ml, about 7 ml to about 14 ml, 7 ml to about 9.8 ml, about 7.112 ml to about 9.296 ml; and a surface area 192 $cm^2$ based on the above ranges of thickness could have volumes ranging from about 9.6 ml to about 96 ml, about 9.6 ml to about 19.2 ml, 9.6 ml to about 13.4 ml, about 0.754 ml to about 12.680 ml.

In the embodiment of illustrated in FIG. 1 a square would have sides 105, 107, 110 and 112 approximately equal in dimensions while a rectangle would have sides 106 and 110 approximately equal in dimensions along with sides 107 and 112 approximately equal, but the dimensions of sides 106 and 110 may not always be equal to the dimension of sides 107 and 112. In other embodiments, the dimensions of any one of sides 106, 107, 110 and 112 may be equal to the dimensions of the other sides.

Figure 2A:
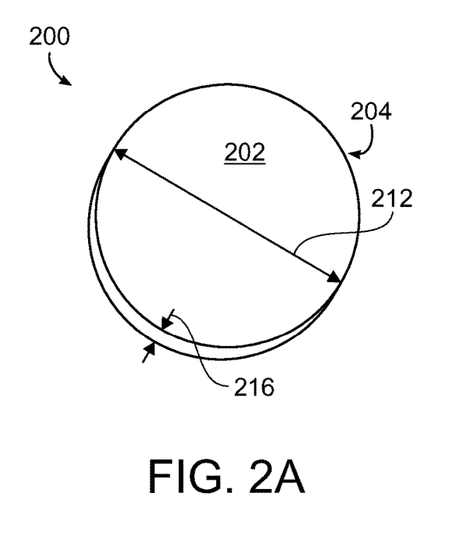
FIGS. 2A and 2B are perspective views of other embodiments of the present disclosure.
Figure 2B:
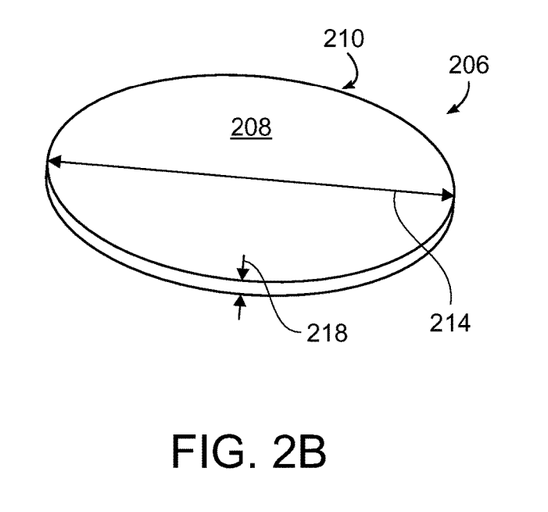

Other embodiment shapes can also include a circle 200 illustrated in FIG. 2A having a generally circular shape with surface areas 202 and 204 on opposing sides thereof or an ellipse 206 illustrated in FIG. 2B and with surface areas 208 and 210 on opposing sides thereof. Diameter 212 for FIG. 2A and diameter 214 for FIG. 2B can range from about 3 cm to about 16 cm including each surface area ranging from about 7 $cm^2$ to about 201 $cm^2$, a diameter ranging from about 4.2 cm to about 6.5 cm including each surface area ranging from about 14 $cm^2$ to about 33 $cm^2$, a diameter ranging from about 10 cm to about 14 cm including each surface area ranging from about 78 $cm^2$ to about 154 $cm^2$ and a diameter ranging from about 12 cm to about 16 cm including each surface area ranging from about 113 $cm^2$ to about 201 $cm^2$ The thickness 216 in circle 200 in FIG. 2A and thickness 218 ellipse 206 in FIG. 2B can range from about 0.05 cm to about 0.5 cm, about 0.05 cm to about 0.1 cm, about 0.05 cm to about 0.07 cm, about 0.0508 to about 0.06604 cm.

Figure 3A:
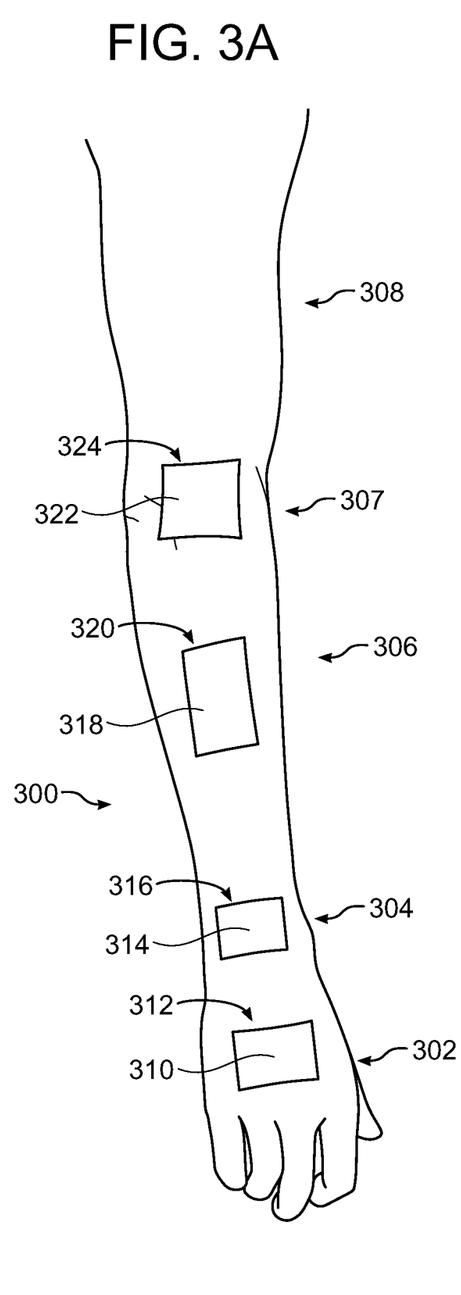
FIGS. 3A to 3F illustrate an exemplary implementation of the aspects of the disclosed embodiments.
Figure 3B:
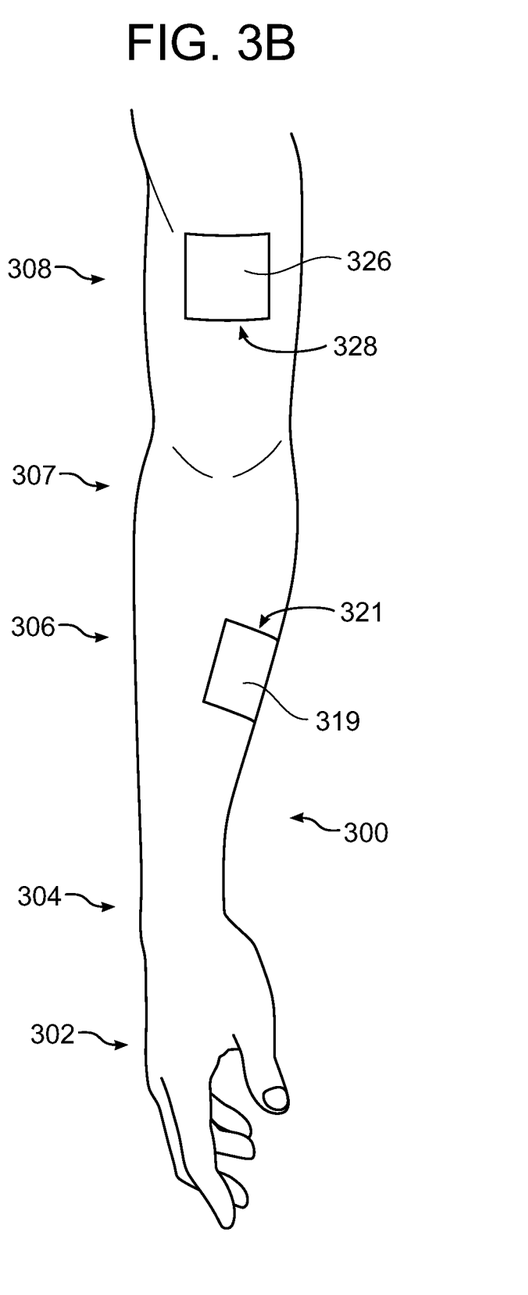

Embodiments of the present disclosure are intended to be placed on the skin surface of a body part or body parts or portions thereof where a person is experiencing pain and/or inflammation resulting from, for example, injury or other physical diseases, stresses or conditions. Non-limiting exemplary embodiments showing possible placement are illustrated in FIGS. 3A to 3F. FIGS. 3A and 3B show a top view and side view, respectively, of an arm 300 including a hand 302, wrist 304, forearm 306, elbow area 307 and upper arm 308. One of the embodiments of the present disclosure 310 can be positioned against the hand 302 at 312. An alternative is an embodiment of the present disclosure 314 can be positioned against the wrist 304 at 316. An alternative is an embodiment of the present disclosure 318 can be positioned against the forearm 306 at 320. An alternative is an embodiment of the present disclosure 319 can be positioned against the lower part of the forearm 306 at 321. An alternative is an embodiment of the present disclosure 322 can be positioned against the elbow area 307 at 324. An alternative is an embodiment of the present disclosure 326 can be positioned against the upper arm 308 at 328.

Figure 3C:
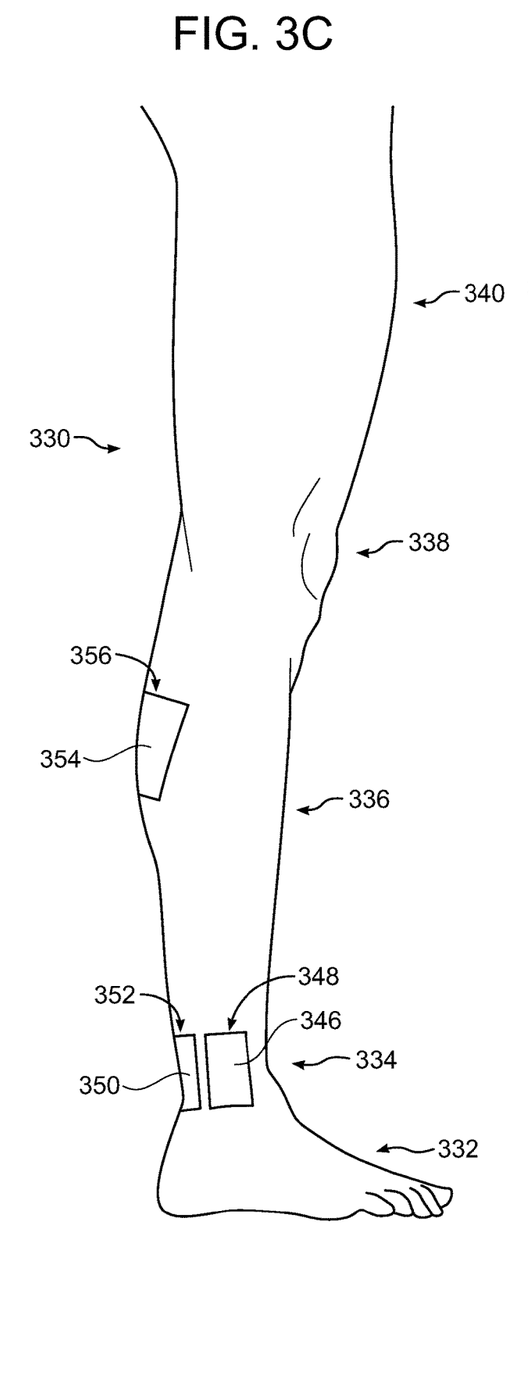
Figure 3D:
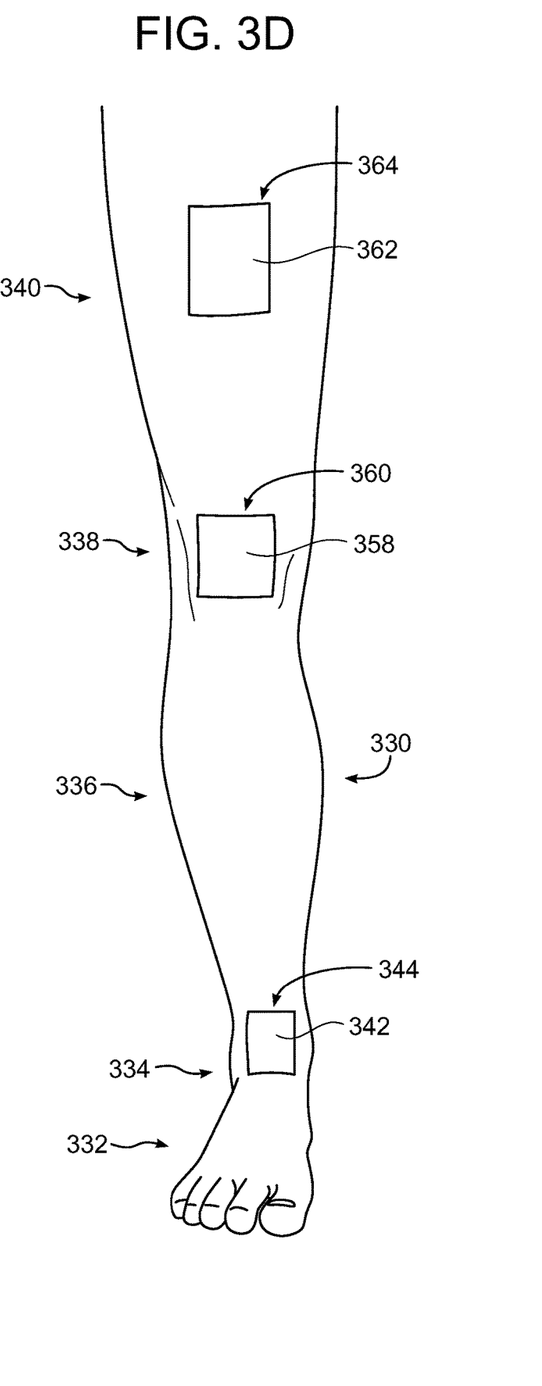

FIGS. 3C and 3D show a side view and front view, respectively, of a leg 330 including a foot 332, ankle area 334, calf 336, knee area 338 and upper leg 340. One of the embodiments of the present disclosure 342 can be positioned against the front of the ankle area 334 at 344. An alternative is an embodiment of the present disclosure 346 can be positioned against the side of the ankle area 334 at 348. An alternative is an embodiment of the present disclosure 350 can be positioned against the back of the ankle area 334 (e.g. against the Achilles tendon) at 352. An alternative is an embodiment of the present disclosure 354 can be positioned against the side of the back of the calf 336 at 356. An alternative is an embodiment of the present disclosure 358 can be positioned against the knee area 338 at 360. An alternative is an embodiment of the present disclosure 362 can be positioned against the front of the upper leg 340 at 364.

Figure 3E:
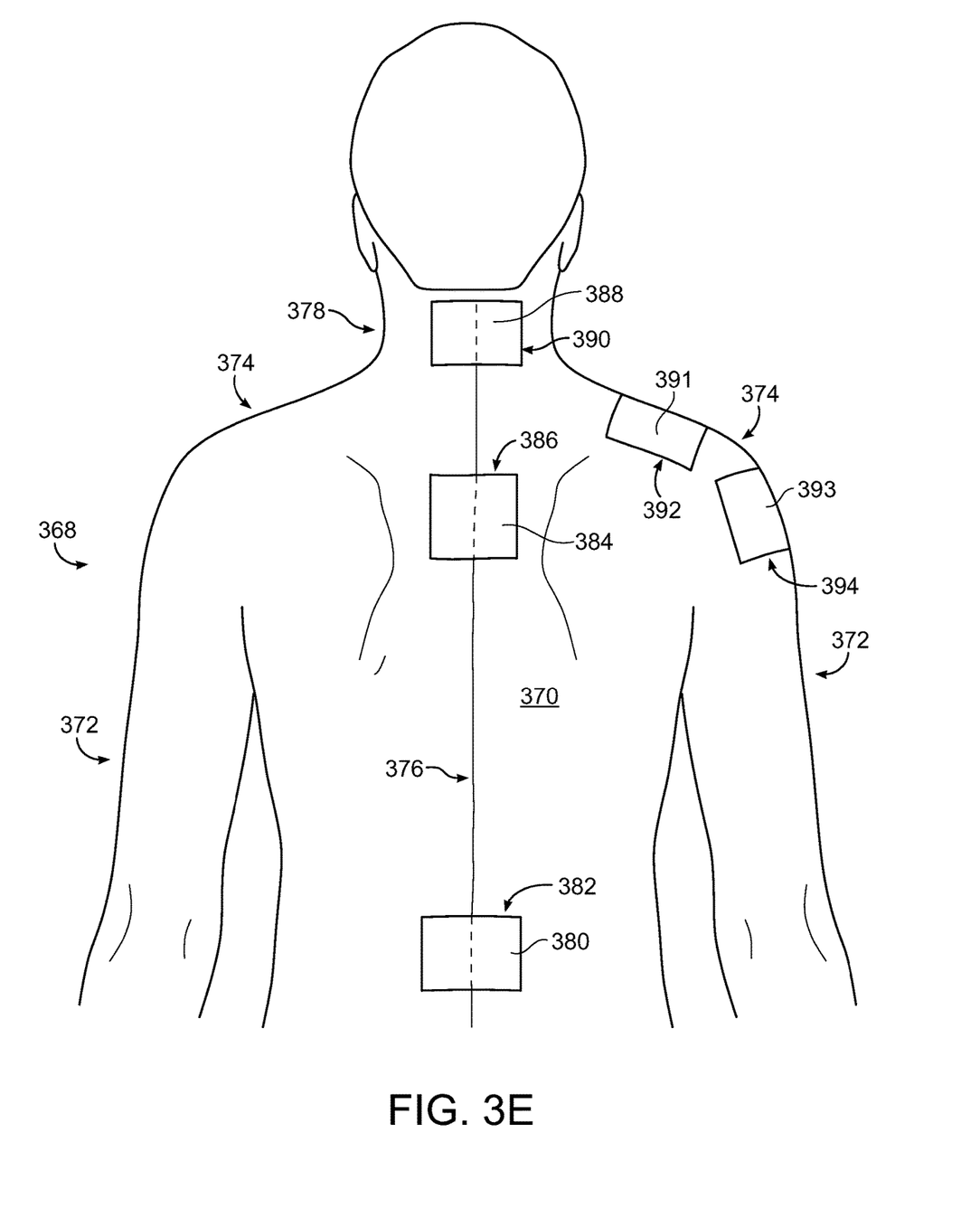

FIG. 3E shows a rear view of an upper torso 368 including back 370, arms 372, shoulder area 374, spinal/backbone area 376 and neck 378. One of the embodiments of the present disclosure 380 can be positioned against the lower region of the back 370 adjacent the spinal/backbone area 376 at 382. An alternative is an embodiment of the present disclosure 384 can be positioned against the upper region of the back 370 adjacent the spinal/backbone area 376 at 386. An alternative is an embodiment of the present disclosure 388 can be positioned against the back of the neck 378 (e.g. against the spinal/backbone area 376) at 390. An alternative is an embodiment of the present disclosure 391 can be positioned against the upper area of the shoulder area 374 at 392. An alternative is an embodiment of the present disclosure 393 can be positioned against the lower area of the shoulder area 374 at 394.

Figure 3F:
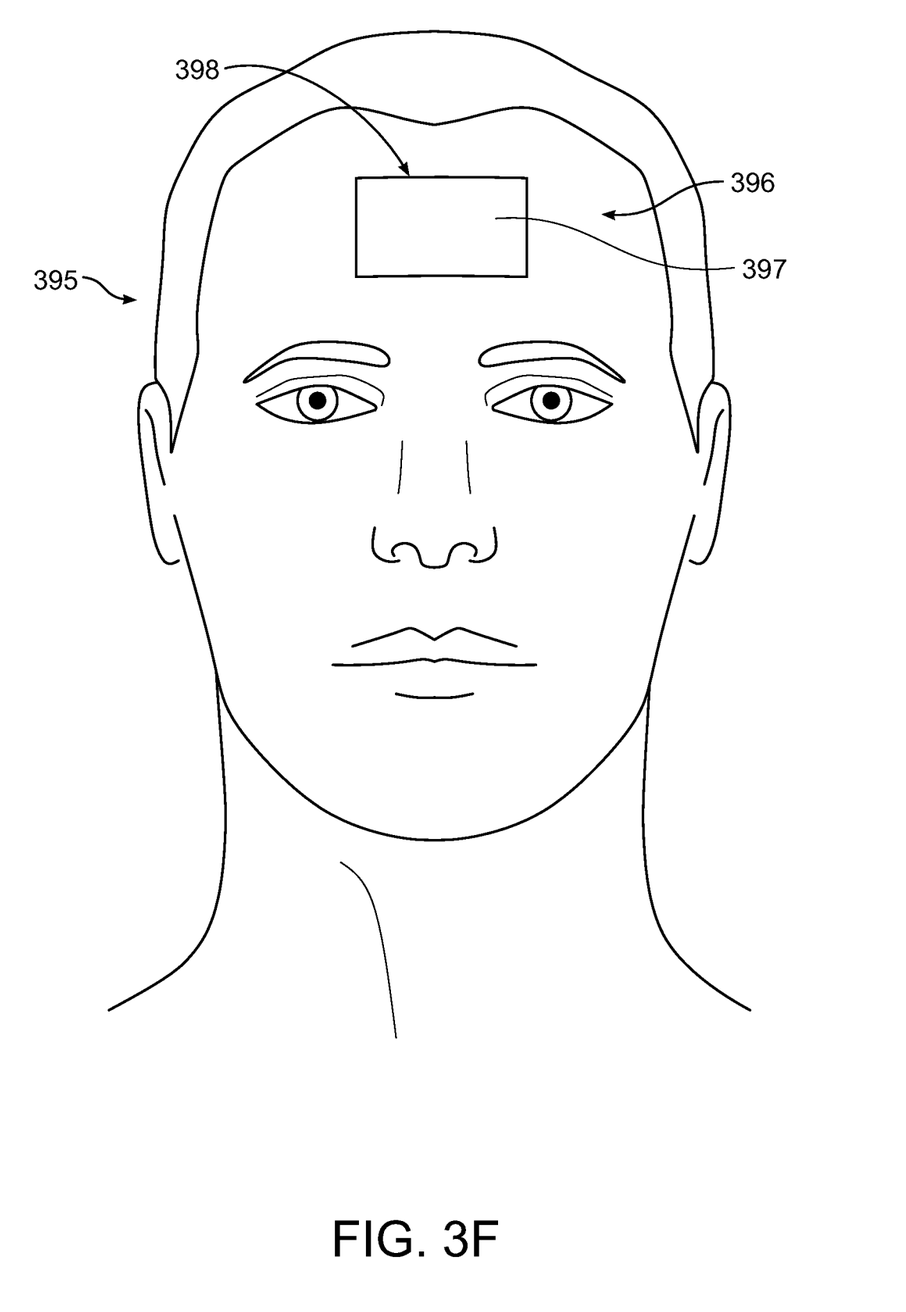

FIG. 3F shows a front view of a head 395 including a forehead 396. One of the embodiments of the present disclosure 397 can be positioned against the forehead 396 at 398.

Although all surfaces of the embodiments of the present disclosure can be applied to the skin surface of body parts or portions thereof to administer the agents included therein (e.g., CBD and menthol) for transdermal delivery into and through the tissues of the skin surface to bring about the intended local and/or systemic effect, the largest surfaces (e.g., surface areas 102 and 104 in FIG. 1, in FIG. 2A with surface areas 202 and 204 and in FIG. 2B and with surface areas 208 and 210) should preferably be placed against those skin surfaces including the embodiments of FIGS. 3A to 3F.

Non-limiting examples of injuries or other physical diseases or conditions causing pain and/or inflammation for which embodiments of the present disclosure can be used to reduce or lessen the pain and/or inflammation can include arthritis conditions (e.g., osteo, rheumatoid, psoriatic, fibromyalgia, etc.), head pain (e.g., concussion, head ache, migraine), orthopedic injuries or conditions (e.g., bone fracture or break; dislocated joint or bone; torn, stressed or strained ligament or tendon; bruising or trauma to tissue; back or spinal pain or herniated disc; tendonitis; gout, bursitis), muscles aches and pains (e.g., from stress and physical exertion) and post-surgery recovery (e.g., recovery from orthopedic surgery to repair a broken bone, back condition such as herniated disk or torn ligament, orthoscopic surgery.

The hydrogel compositions of the present disclosure may also include an adhesive composition on one side thereof (e.g., one of the surface areas of the above embodiments). In manufacturing such systems of an embodiment, the hydrogel adhesive composition may be cast or extruded onto a backing layer or release liner and once the backing layer or release liner is removed will serve as the skin-contacting face of the system and act as an active agent reservoir. Alternatively, the hydrogel composition may be used as an active agent reservoir within the interior of such a system, with a conventional skin adhesive laminated thereto to affix the system to a surface of the body part of a patient, the body part that is experiencing pain and/or inflammation. In such embodiments including a reservoir, the cannabinoid, for example, full spectrum hemp oil, could be in the reservoir and the menthol in the hydrogel housing the reservoir, where each reservoir for the full spectrum hemp oil and menthol is the same or different.

Cannabinoids are an active agent and a class of chemical compounds that can be derived from plants (phytocannabinoids) or synthetically produced. Cannabinoids can have local and systemic analgesic, pain relieving, pain treating and anti-inflammatory therapeutic properties. Cannabinoids may also have other medical benefits and/or be useful in treating other medical conditions including, for example, reduction of anxiety and depression, reduction of symptoms like nausea, vomiting and pain related to cancer treatments, reduction of acne, protection of the neural system and benefits for the heart and circulatory system by the lowering of blood pressure. Cannabinoids can also have therapeutic value as a nutrient and can be included in composition and method embodiments of the present disclosure in an effective amount to perform that function.

Examples of phytocannabinoids include Cannabidiol (CBD) including, for example, CBD oil, Cannabinol (CBN) and tetrahydrocannabinol (THC), the latter being a known psychotropic compound and the first two being non-psychotropic. Cannabis and hemp plants can exhibit wide variation in the quantity and type of cannabinoids they produce. Selective breeding of the plants can be used to control the genetics of plants and modify the cannabinoids produced by the plant. For example, there are strains that are used as fiber (commonly called hemp) and, as a result, have been bred such that they are low in psychoactive chemicals like THC. Such strains (e.g., hemp) used in medicine are, for example, often bred for high CBD content and cannabinoids included herein (unless otherwise stated) have minimal levels of THC (less than 0.3%). Examples of topical, transdermal and/or pharmaceutically effective cannabinoids include CBD (for example, full spectrum hemp oil). Cannabinoid, including, for example, phytocannabinoids including CBD, can be in an amount of about 0.1 wt % to about 10 wt %, 0.1 wt % to about 1 wt %, about 0.5 wt % to about 6 wt %, about 2 wt %, about 2.1 wt %, about 4 wt %. CBD can be in an amount of 0.1 wt % to about 10 wt %, about 0.5 wt % to about 5 wt %, about 0.5 wt % to about 2 wt % %, about 2 wt %, about 2.1 wt %, about 4 wt %. Full spectrum CBD or hemp oil can be in an amount of about 0.1 wt % to about 10 wt %, 0.1 wt % to about 1 wt %, about 0.5 wt % to about 6 wt %, about 2 wt %, about 2.1 wt %, about 4 wt %. Unit dosage formulations of the embodiments of the present disclosure can include cannabinoid, for example, a phytocannabinoid (including for example, CBD) in the amount of about 2 mg. to about 195 mg., about 14 mg. to about 100 mg., about 14 mg. to about 80 mg., about 70 mg. to about 195 mg., about 10 mg. to about 15 mg, about 70 mg. to about 80 mg, about 1900 mg. to about 195 mg, about 14 mg, about 77 mg, about 193 mg. Unit dosage formulations of the embodiments of the present disclosure can include CBD in the amount of about 2 mg. to about 195 mg., about 14 mg. to about 100 mg., about 14 mg. to about 80 mg., about 70 mg. to about 195 mg., about 10 mg. to about 15 mg, about 70 mg. to about 80 mg, about 1900 mg. to about 195 mg, about 14 mg, about 77 mg, about 193 mg. Unit doses of full spectrum hemp oil can include an amount of about 2 mg. to about 195 mg., about 14 mg. to about 100 mg., about 14 mg. to about 80 mg., about 70 mg. to about 195 mg., about 10 mg. to about 15 mg, about 70 mg. to about 80 mg, about 1900 mg. to about 195 mg, about 14 mg, about 77 mg, about 193 mg. Unit dosage formulations of the embodiments of the present disclosure can include cannabinoid, for example, a phytocannabinoid (including for example, CBD) or full spectrum hemp oil in the amount of about 5 mg./ml. to about 40 mg./ml., about 5 mg./ml. to about 20 mg./ml., about 9 mg. to about 16 mg./ml., about 9 mg./ml., about 15 mg./ml. Unit dosage formulations of the embodiments of the present disclosure can include CBD in the amount of about 1 mg./ml. to about 50 mg./ml, about 5 mg./ml. to about 40 mg./ml., about 5 mg./ml. to about 20 mg./ml., about 9 mg./ml to about 16 mg./ml., about 9 mg./ml., about 15 mg./ml. Unit dosage formulations of the embodiments of the present disclosure can include full spectrum CBD oil in an amount of about 5 mg./ml. to about 40 mg./ml, about 5 mg./ml. to about 20 mg./ml, about 9 mg./ml to about 16 mg./ml, about 9 mg./ml, about 15 mg./ml.

Unit dosage formulations of the embodiments of the present disclosure can include cannabinoid, for example, a phytocannabinoid (including for example, CBD) in the amount per unit of surface area (e.g., surface areas 102 and 104 in FIG. 1, in FIG. 2A with surface areas 202 and 204 and in FIG. 2B and with surface areas 208 and 210) of about 0.1 mg./cm$^2$ to about 2 mg./cm$^2$, about 0.5 mg./cm$^2$ to about 1 mg./cm$^2$, about 0.5 mg./cm$^2$ to about 0.6 mg./cm$^2$, about 0.5 mg./cm$^2$, about 0.53 mg./cm$^2$, about 0.5 mg./cm$^2$, about 1 mg./cm$^2$. Unit dosage formulations of the embodiments of the present disclosure can include CBD in the amount of about 0.1 mg./cm$^2$ to about 2 mg./cm$^2$, about 0.5 mg./cm$^2$ to about 1 mg./cm$^2$, about 0.5 mg./cm$^2$ to about 0.6 mg./cm$^2$, about 0.5 mg./cm$^2$, about 0.53 mg./cm$^2$, about 0.5 mg./cm$^2$, about 1 mg./cm$^2$. Unit dosage formulations of the embodiments of the present disclosure can include full spectrum CBD oil in an amount of about 0.1 mg./cm$^2$ to about 2 mg./cm$^2$, about 0.5 mg./cm$^2$ to about 1 mg./cm$^2$, about 0.5 mg./cm$^2$ to about 0.6 mg./cm$^2$, about 0.5 mg./cm$^2$, about 0.53 mg./cm², about 0.5 mg./cm², about 1 mg./cm². An effective amount of cannabinoid includes an analgesic, pain relieving, pain treating or anti-inflammatory amount of cannabinoid.

Cannabinoids, for example, CBD can have a local and/or a systemic effect and may reduce pain imparting and regulating the endocannabinoid (neurotransmitter of the nervous system) receptor activity. The subsequent body functions that may be regulated include pain, sleep, appetite and immune system response (through, at least, in part, by reducing inflammation).

For the purpose of the present disclosure, the word "cannabinoid" refers to one or more cannabinoids or cannabinoid compounds or oils or extracts from plants (for example, hemp including hemp oil and full spectrum CBD or full spectrum hemp oil, Cannabis sativa seed oil, etc.) that include one or a plurality of phytocannabinoids.

Full spectrum hemp oil is oil derived from the entire plant except the flower (which contains THC) and can have over 85 phytocannabinoids which can have a positive synergistic effect as compared to compositions having fewer cannabinoids. There may also be benefits to other components of it (e.g., terpenes). Such benefits and effect may include faster penetration and/or permeation of the therapeutic components thereof. Full spectrum hemp oil can include full spectrum hemp oil that has been purified to include less than the below stated amounts of one or more of the following impurities:

Aflatoxins B1, 82, G1, G2 (fats, oils, lecithin, egg powder): <0.1 µg/kg of each of Aflatoxin B1, Aflatoxin B2, Aflatoxin G1 and Aflatoxin G2, Sum of all positive Aflatoxins <0.4 µg/kg.

GlyphosatelAMPAiGlufosinate: <0.1 mg/kg of each of Glufosinate, Glyphosate and Aminomethylphosphonic acid (AMPA)

Mercury: <0.02 mg/kg
Arsentic: <0.03 mg/kg
Cadmium: <0.01 mg/kg
Lead: <0.05 mg/kg.

Embodiments of the present disclosure may also optionally include an effective amount of THC and other forms of THC such as THCA, THCV. delta-8 THC.delta-9 THC etc. Unit dosage formulations of the embodiments of the present disclosure can include THC in the amount of about 0.1 mg. to about 10 mg., about 1 mg. to about 10 mg., about 4 mg. to about 6 mg. about 5 mg. In addition to the other benefits that can be provided by other cannabinoids, THC may relieve stress and be a sleeping aid.

Menthol is an active agent and an organic compound that can be made synthetically or obtained from mint oils such as corn mint and peppermint. Medicinally, it been found that menthol can have anesthetic (e.g., local) by, for example, blocking nerve signal transmission) and counterirritant properties as well as anti-inflammatory properties (e.g., systemic and local) as well as a cooling effect when administered topically to a patient. Furthermore, menthol is a vasodilator that can accelerate the transport of active in the circulatory system. In general, the action of local anesthetics can restrict to the site of application and rapidly reverses upon diffusion from the site of action in the nerve. Local anesthetics can also serve an important function in providing peripheral pain relief. Topical administration of pain-relieving anesthetics can provide important advantages over systemic or local, non-topical administration. Menthol can be in an amount of about 1 wt % to about 10 wt %, about 5 wt % to about 10 wt %, about 5 wt %, about 6 wt %, about 8 wt %. Unit dosage formulations of the embodiments of the present disclosure can include menthol in the amount of about 2 mg. to about 400 mg., about 30 mg. to about 40 mg., about 210 mg. to about 220 mg., about 380 mg. to about 390 mg., about 36 mg., about 217 mg., about 386 mg. Unit dosage formulations of the embodiments of the present disclosure can include menthol in the amount of about 1 mg./ml. to about 40 mg./ml, about 10 mg./ml. to about 35 mg./ml., about 20 mg./ml. to about 30 mg./ml., about 23 mg./ml to about 27 mg./ml., about 26 mg./ml to about 30 mg./ml., about 23 mg./ml., about 26 mg./ml, about 30 mg./ml. Unit dosage formulations of the embodiments of the present disclosure can include menthol in the amount per unit of surface area (e.g., surface areas 102 and 104 in FIG. 1, in FIG. 2A with surface areas 202 and 204 and in FIG. 2B and with surface areas 208 and 210) of about 0.1 mg./cm² to about 3 mg./cm², about 1 mg./cm² to about 2 mg./cm², about 1.3 mg./cm² to about 1.6 mg./cm², about 1.33 mg./cm², about 1.55 mg./cm², about 2 about 1.33 mg./cm². An effective amount of menthol includes an anesthetic, pain reducing (e.g., analgesic) or anti-inflammatory effective amount of menthol.

Menthol may be stabilized using methods know in the art, such as, for example, mixing it with about 0.1 wt % to about 10 wt %, about 0.5 wt % to about 5 wt % of a surfactant including edible nonionic surfactants and ionic surfactants, such as, for example, sucrose fatty acid ester, polysorbate (e.g., polysorbate 80), hydrogenated castor oil (e.g., polyoxyethylene hydrogenated castor oil), cocamidopropyl betaine, etc.

The aspects of the present disclosure also relate to embodiments including compositions, methods of making and methods of using included herein which also comprise the menthol component included in embodiments of the present disclosure in a stabilized menthol composition as well as methods of making and using them including a mixture of (a) menthol and (b) a menthol stabilizer compound including undecylenic acid methyl ester or undecylenic acid or a salt (preferably a pharmaceutically acceptable salt) thereof where the menthol in the stabilized menthol compositions is less susceptible to volatizing into a gas and remains in a form that can be administered in a composition in an amount closer to the amount originally included in the composition when formulated with less menthol volatizing away (i.e., lowering the rate of volatilization of the menthol from what it would be for menthol alone) from the original concentration and, thus, lowering the original concentration and diminishing the amount of the menthol originally added.

Undecylenic acid salts, including pharmaceutically acceptable salts may include, for example, inorganic acid addition, hydrochloride salts, sulfate and phosphate salts; and organic acid addition salts, such as alkyl sulfonate, arylsulfonate, acetate, maleate, fumarate, tartrate, citrate and lactate and metal salts including alkali metal salts, such as lithium salt, sodium salt and potassium salt and alkaline earth metal salts, such as magnesium salt and calcium salt, strontium salt, aluminum salt and zinc salt, and other multivalent salts such as for example, zirconium, iron, copper, silver, bismuth etc. Additionally primary secondary, and tertiary amine salts, organic and inorganic, mono and polyamines compounds could utilized. Examples include compounds such as urea, and amino acids such as lysine, histidine, arginine etc, could be utilized.

The stabilized menthol compositions can made by mixing together (a) menthol and (b) a menthol stabilizer compound in a ratio of (a) about 1 molar part menthol to (b) the amount of one or more than one of the menthol stabilizer compounds (undecylenic acid methyl ester, undecylenic acid or a salt of undecylenic acid, including mixtures thereof) of from about 0.005 molar part to about 1.00 molar part, about 0.010 molar part to about 0.750 molar part, about 0.020 molar part to about 0.50 molar part, about 0.050 molar part to about 0.250 molar part, or about 0.10 molar part. It is believed that the menthol stabilizer compounds (undecylenic acid methyl ester, undecylenic acid or a salt of undecylenic acid, including mixtures thereof) and menthol may associate to form a menthol analog where the menthol analog's vapor pressure becomes lower than menthol itself. As a result of having a lower vapor pressure, the menthol component of the menthol analog volatizes as a lower rate than menthol by itself.

One possible explanation for the stabilization of menthol by the compound of formula (I) may be that the menthol associates with the alkenyl side chain of the menthol stabilizer compounds (undecylenic acid methyl ester, undecylenic acid or a salt of undecylenic acid, including mixtures thereof) may provide a molecular attraction connecting the menthol stabilizer compounds (undecylenic acid methyl ester, undecylenic acid or a salt of undecylenic acid, including mixtures thereof) and a menthol molecule, such that more than one menthol molecule may associate with a molecule of one of the menthol stabilizer compounds (undecylenic acid methyl ester, undecylenic acid or a salt of undecylenic acid, including mixtures thereof).

The stabilized menthol compositions including menthol and at least one of the menthol stabilizer compounds (undecylenic acid methyl ester, undecylenic acid or a salt of undecylenic acid, including mixtures thereof) can be also be made first by dissolving menthol in a pharmaceutically acceptable suitable solvent such as, for example, as a low, medium, or long chain triglyceride. Examples of such solvents are coconut oil, olive oil, palm oil, hemp oil and castor oil. Still other acceptable solvents, such as alcohols, ethers and polyalcohols, for example, propylene glycol, butylene glycol, and polyethylene glycols (PEGs) can also be used. The desired amount of at least one of the menthol stabilizer compounds (undecylenic acid methyl ester, undecylenic acid or a salt of undecylenic acid, including mixtures thereof) is then added to that mixture. Such compositions that include menthol, solvent and one or more than one of the menthol stabilizer compounds (undecylenic acid methyl ester, undecylenic acid or a salt of undecylenic acid, including mixtures thereof) may be made where the mixture of the these ingredients includes a molar ratio of about one molar part menthol to a range of from about 0.0050 molar part to about 1.00 molar part, about 0.010 molar part to about 0.750 molar part, about 0.020 molar part to about 0.50 molar part, about 0.050 molar part to about 0.250 molar part, or about 0.10 molar part of at least one of the menthol stabilizer compounds (undecylenic acid methyl ester, undecylenic acid or a salt of undecylenic acid, including mixtures thereof), preferably a molar ratio of about one molar part menthol to at most about 0.50 molar part, at most about 0.250 molar part or at most about 0.10 molar part of one or more than one of the menthol stabilizer compounds (undecylenic acid methyl ester, undecylenic acid or a salt of undecylenic acid, including mixtures thereof). Such mixtures of menthol, solvent and menthol stabilizer compounds (undecylenic acid methyl ester, undecylenic acid or a salt of undecylenic acid, including mixtures thereof) may be used when smaller amounts of menthol need to be stabilized (where the amount of menthol stabilizer compound (undecylenic acid methyl ester, undecylenic acid or a salt of undecylenic acid, including mixtures thereof) to be mixed with the menthol is so small that there isn't enough of it to dissolve the menthol).

Both menthol stabilized compositions (i.e., where the menthol is first dissolved in a solvent then dissolved in a menthol stabilizer compound (undecylenic acid methyl ester, undecylenic acid or a salt of undecylenic acid, including mixtures thereof) or where the menthol is directly dissolved in a menthol stabilizer compound (undecylenic acid methyl ester, undecylenic acid or a salt of undecylenic acid, including mixtures thereof)) can be used in orally administrated and non-orally administrated compositions (e.g., non-orally topically administrated compositions (e.g., place on the skin or other external tissues)). However, the menthol stabilizer compounds (undecylenic acid methyl ester, undecylenic acid or a salt of undecylenic acid, including mixtures thereof) can have a bitter taste. The dissolving of the menthol in solvent prior to the addition of at least one of the menthol stabilizer compounds (undecylenic acid methyl ester, undecylenic acid or a salt of undecylenic acid, including mixtures thereof) is preferably used in menthol containing therapeutic compositions to be administered orally because by first dissolving the menthol in a suitable solvent, less of the menthol stabilizer compounds (undecylenic acid methyl ester, undecylenic acid or a salt of undecylenic acid, including mixtures thereof) may be used, thus lessening the bitter taste of the menthol stabilized composition(undecylenic acid methyl ester, undecylenic acid or a salt of undecylenic acid, including mixtures thereof) and the final product in which it is included that is imparted by the menthol stabilizer compound (undecylenic acid methyl ester, undecylenic acid or a salt of undecylenic acid, including mixtures thereof).

The aspects of the present disclosure also relate to hydrogels, for example, a hydrous hydrogel, for the delivery of, for example, pharmaceutical compositions, including analgesic pharmaceutical compositions, that contain a pharmaceutically effective amount of a pharmaceutically acceptable and effective cannabinoid and a pharmaceutically effective amount of menthol and topical compositions, including topical analgesic compositions, that contain a pharmaceutically topical effective amount of a topically acceptable and effective cannabinoid and a pharmaceutically topical effective amount of menthol.

An embodiment of the present disclosure relates to a hydrous hydrogel comprising an aqueous base, a biocompatible polymer, a polyalcohol, a pharmaceutically and/or topically effective amount of a pharmaceutically and topically acceptable and effective cannabinoid, for example, a phytocannabinoid or full spectrum CDB or hemp oil, and a pharmaceutically and/or topically effective amount of a pharmaceutically and topically acceptable and effective menthol.

Another embodiment of the present disclosure relates to a hydrous hydrogel analgesic composition comprising an aqueous base, a biocompatible polymer, a polyalcohol, a pain reducing (e.g., analgesic and/or anesthetic) and/or anti-inflammatory pharmaceutically and topically effective amount of a pharmaceutically and topically acceptable and effective cannabinoid, for example, a phytocannabinoid or full spectrum CDB or hemp oil, and a pain reducing (e.g., analgesic and/or anesthetic) and/or anti-inflammatory pharmaceutically and topically effective amount of a pharmaceutically and topically acceptable and effective menthol.

Another embodiment of the present disclosure relates to a hydrous hydrogel composition comprising an aqueous base, a pharmaceutically acceptable biocompatible polymer, a pharmaceutically acceptable polyalcohol, a pain reducing (e.g., analgesic and/or anesthetic) and/or anti-inflammatory pharmaceutically and topically effective amount of a pharmaceutically and topically acceptable and effective cannabinoid, for example, a phytocannabinoid, and a pain reducing (e.g., analgesic and/or anesthetic) and/or anti-inflammatory pharmaceutically and topically effective amount of a pharmaceutically and topically acceptable and effective menthol.

Another embodiment of the present disclosure relates to a hydrous hydrogel analgesic and/or anti-inflammatory composition comprising an aqueous base, a pharmaceutically and topically pharmaceutically acceptable biocompatible polymer, a pharmaceutically and topically acceptable polyalcohol, a pain reducing (e.g., analgesic and/or anesthetic) and/or anti-inflammatory pharmaceutically and topically effective amount of a pharmaceutically and topically acceptable and effective cannabinoid, for example, a phytocannabinoid or full spectrum CDB or hemp oil, and a pain reducing (e.g., analgesic and/or anesthetic) and/or anti-inflammatory pharmaceutically and topically effective amount of a pharmaceutically and topically acceptable and effective menthol.

The aqueous base can be, for example, water. Water should be deionized and pharmaceutically acceptable free of impurities and microbiological organisms that could harm the user. Total water content (including residual water present in other ingredients) can be in an amount of about 70 wt % to about 95 wt %, about 80 wt % to about 95 wt %, about 82 wt % to about 92 wt %, about 83 wt % to about 91 wt %, about 83 wt %, about 87 wt %, about 91 wt %.

Suitable biocompatible polymers that act as gelling, thickening and/or stabilizing agents can include for example of, including pharmaceutically acceptable biocompatible polymers, can include gelatin, agar, sodium carboxymethylcellulose, pectin, sodium alginate, sodium/calcium alginate, polylactic acid, chitosan, carageenan, xanthan, gellan, polyaspartic acid, polyglutamic acid, hyaluronic acid or salts or derivatives thereof. A preferred biocompatible polymer is carageenan. Biocompatible polymer, such as, for example, carrageenan, including iota carrageenan, can be in an amount of about 0.5 wt % to about 10 wt %, about 0.5 wt % to about 1 wt %, about 0.75 wt % to about 1 wt %, about 0.75 wt %. Some of the biocompatible polymers may also stabilize the menthol component of embodiments of the present disclosure.

Suitable polyalcohols that can act as a humectant to, for example, stabilize oil in water compositions and retain water, include pharmaceutically acceptable biocompatible polyalcohols, can include alcohols containing 2 to 10 carbon atoms and 2 to 7 hydroxyl groups including, for example, ethylene glycol, 1,2-propylene glycol, 1,4-butylene glycol, glycerine, glycerine betaine, erythrit (meso-1,2,3,4-Butantetrol), sorbit, mannit, methylglucoside, diglycerine, triglycerine and/or pentaerythrit as well as sodium lactate. Polyalcohols, such as for example, glycerin can be in an amount of about 1 wt % to about 25 wt %, about 1 wt % to about 4 wt %, about 2 wt % to about 3 wt %, about 3 wt %.

An embodiment of the present disclosure relates to a hydrogel composition comprising an aqueous base, glycerin, carageenan, a pharmaceutically effective amount of a pharmaceutically and/or topically acceptable and effective cannabinoid, for example, a phytocannabinoid or full spectrum CDB or hemp oil, and a pharmaceutically and/or topically acceptable effective amount of a pharmaceutically acceptable and effective menthol.

Another embodiment of the present disclosure relates to a hydrogel analgesic composition comprising an aqueous base, glycerin, carageenan, a pain reducing (e.g., analgesic and/or anesthetic) and/or anti-inflammatory pharmaceutically and/or topically effective amount of a pain reducing (e.g., analgesic and/or anesthetic) and/or anti-inflammatory pharmaceutically and/or topically acceptable and effective cannabinoid, for example, a phytocannabinoid, and a pain reducing (e.g., analgesic and/or anesthetic) and/or anti-inflammatory pharmaceutically and/or topically effective amount of a pain reducing (e.g., analgesic and/or anesthetic and/or anesthetic) and/or anti-inflammatory pharmaceutically and/or topically acceptable and effective menthol.

In a one embodiment of the present disclosure, the hydrogel comprises an aqueous base (including water) in an amount of 70 wt % to about 95 wt %, about 80 wt % to about 95 wt %, about 82 wt % to about 92 wt %, about 83 wt % to about 91 wt %, about 83 wt %, about 87 wt %, about 91 wt %, the biocompatible polymer (including carageenan) in an amount of about 0.5 wt % to about 5 wt %, about 0.5 wt % to about 1 wt %, about 0.75 wt % to about 1 wt %, about 0.75 wt %, the polyalcohol (including glycerine) in an amount of about 1 wt % to about 5 wt %, about 1 wt % to about 4 wt %, about 2 wt % to about 3 wt %, about 3 wt %; cannabinoid, for example, phytocannabinoids of full spectrum CBD or hemp oil, in an amount of about 0.1 wt % to about 10 wt %, 0.1 wt % to about 1 wt %, about 0.5 wt % to about 6 wt %, about 2 wt %, about 2.1 wt %, about 4 wt %. including unit dosage amounts of about 2 mg. to about 195 mg., about 14 mg. to about 100 mg., about 14 mg. to about 80 mg., about 70 mg. to about 195 mg., about 10 mg. to about 15 mg, about 70 mg. to about 80 mg, about 1900 mg. to about 195 mg, about 14 mg, about 77 mg, about 193 mg, about 5 mg./ml. to about 40 mg./ml., about 5 mg./ml. to about 20 mg./ml., about 9 mg. to about 16 mg./ml., about 9 mg./ml., about 15 mg./ml; and menthol in an amount of about 1 wt % to about 10 wt %, about 5 wt % to about 10 wt %, about 5 wt %, about 6 wt %, about 8 wt % including unit dosage amounts of 2 mg. to about 400 mg., about 30 mg. to about 40 mg., about 210 mg. to about 220 mg., about 380 mg. to about 390 mg., about 36 mg., about 217 mg., about 386 mg, about 1 mg./ml. to about 40 mg./ml, about 10 mg./ml. to about 35 mg./ml., about 20 mg./ml. to about 30 mg./ml., about 23 mg./ml to about 27 mg./ml., about 26 mg./ml to about 30 mg./ml., about 23 mg./ml., about 26 mg./ml, about 30 mg./ml.

In another embodiment of the present disclosure, the hydrogel comprises water in an amount of 70 wt % to about 95 wt %, about 80 wt % to about 95 wt %, about 82 wt % to about 92 wt %, about 83 wt % to about 91 wt %, about 83 wt %, about 87 wt %, about 91 wt %, carageenan in an amount of about 0.5 wt % to about 5 wt %, about 0.5 wt % to about 1 wt %, about 0.75 wt % to about 1 wt %, about 0.75 wt %; glycerin in an amount of about 1 wt % to about 5 wt %, about 1 wt % to about 4 wt %, about 2 wt % to about 3 wt %, about 3 wt %; cannabinoid, for example, phytocannabinoids and full spectrum CBD or hemp oil, in an amount of about 0.1 wt % to about 10 wt %, 0.1 wt % to about 1 wt %, about 0.5 wt % to about 6 wt %, about 2 wt %, about 2.1 wt %, about 4 wt %. Full spectrum hemp oil can be in an amount of 0.1 wt % to about 10 wt %, about 0.5 wt % to about 5 wt %, about 0.5 wt % to about 2 wt % %, about 2 wt %, about 2.1 wt %, about 4 wt % including unit dosage amounts of about 2 mg. to about 195 mg., about 14 mg. to about 100 mg., about 14 mg. to about 80 mg., about 70 mg. to about 195 mg., about 10 mg. to about 15 mg, about 70 mg. to about 80 mg, about 1900 mg. to about 195 mg, about 14 mg, about 77 mg, about 193 mg, about 5 mg./ml. to about 40 mg./ml., about 5 mg./ml. to about 20 mg./ml., about 9 mg.

to about 16 mg./ml., about 9 mg./ml., about 15 mg./ml; and menthol in an amount of about 1 wt % to about 10 wt %, about 5 wt % to about 10 wt %, about 5 wt %, about 6 wt %, about 8 wt % including unit dosage amounts of 2 mg. to about 400 mg., about 30 mg. to about 40 mg., about 210 mg. to about 220 mg., about 380 mg. to about 390 mg., about 36 mg., about 217 mg., about 386 mg, about 1 mg./ml. to about 40 mg./ml, about 10 mg./ml. to about 35 mg./ml., about 20 mg./ml. to about 30 mg./ml., about 23 mg./ml to about 27 mg./ml., about 26 mg./ml to about 30 mg./ml., about 23 mg./ml., about 26 mg./ml, about 30 mg./ml.

The terms "treating" and "effective amount", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neoadjuvant treatment of a subject.

In a further embodiment, a kit is disclosed. One example of such a kit is a kit including a composition or unit dose composition (e.g., a patch or mass of embodiment composition) of one of the embodiments of the present disclosure including multiple unit doses and instructions for use.

Optional ingredients include skin oil cleanser and/or cooling agents such as, for example, denatured alcohol or isopropyl alcohol.

Skin oil cleanser and/or cooling agents, including pharmaceutically acceptable skin oil cleanser and/or cooling agents, can include, for example, alcohols such as denatured alcohol or isopropyl alcohol. One purpose of such a skin oil cleanser and/or cooling agents would be to break-up oil deposits on the skin where the composition is applied where such deposits may interfere with the transdermal passage of the cannabinoid and menthol ingredients into the tissue beneath the skin layer. Skin oil cleanser and/or cooling agents, such as, for example, denatured alcohol can be generally used at levels of from about 0.1 wt % to about 2 wt %, about 0.5 wt % to about 1.5 wt %, about 1 wt % to about 2 wt %, about 1 wt %.

In a one embodiment of the present disclosure, the hydrogel comprises an aqueous base (including water) in an amount of 70 wt % to about 95 wt %, about 80 wt % to about 95 wt %, about 82 wt % to about 92 wt %, about 83 wt % to about 91 wt %, about 83 wt %, about 87 wt %, about 91 wt %, the biocompatible polymer (including carageenan) in an amount of about 0.5 wt % to about 5 wt %, about 0.5 wt % to about 1 wt %, about 0.75 wt % to about 1 wt %, about 0.75 wt %, the polyalcohol (including glycerine) in an amount of about 1 wt % to about 5 wt %, about 1 wt % to about 4 wt %, about 2 wt % to about 3 wt %, about 3 wt %; cannabinoid, for example, phytocannabinoids and full spectrum CBD or hemp oil, in an amount of about 0.1 wt % to about 10 wt %, 0.1 wt % to about 1 wt %, about 0.5 wt % to about 6 wt %, about 2 wt %, about 2.1 wt %, about 4 wt %. CBD can be in an amount of 0.1 wt % to about 10 wt %, about 0.5 wt % to about 5 wt %, about 0.5 wt % to about 2 wt % %, about 2 wt %, about 2.1 wt %, about 4 wt % including unit dosage amounts of about 2 mg. to about 195 mg., about 14 mg. to about 100 mg., about 14 mg. to about 80 mg., about 70 mg. to about 195 mg., about 10 mg. to about 15 mg, about 70 mg. to about 80 mg, about 1900 mg. to about 195 mg, about 14 mg, about 77 mg, about 193 mg, about 5 mg./ml. to about 40 mg./ml, about 5 mg./ml. to about 20 mg./ml, about 9 mg. to about 16 mg./ml, about 9 mg./ml, about 15 mg./ml; menthol in an amount of about 1 wt % to about 10 wt %, about 5 wt % to about 10 wt %, about 5 wt %, about 6 wt %, about 8 wt % including unit dosage amounts of 2 mg. to about 400 mg., about 30 mg. to about 40 mg., about 210 mg. to about 220 mg., about 380 mg. to about 390 mg., about 36 mg., about 217 mg., about 386 mg, about 1 mg./ml. to about 40 mg./ml, about 10 mg./ml. to about 35 mg./ml, about 20 mg./ml. to about 30 mg./ml, about 23 mg./ml to about 27 mg./ml, about 26 mg./ml to about 30 mg./ml, about 23 mg./ml, about 26 mg./ml, about 30 mg./ml; and a skin oil cleanser and/or cooling agent (including denatured alcohol) in an amount of about 0.1 wt % to about 2 wt %, about 1 wt % to about 2 wt %, about 1 wt %.

In another embodiment of the present disclosure, the hydrogel comprises about 3.0 wt % glycerin; about 91 wt % water; about 1.0 wt % denatured alcohol; about 5 wt % menthol (about 36.33 mg; about 23 mg./ml.); and about 2.0 wt % full spectrum CBD or hemp oil (about 14.53 mg; about 9.2 mg./ml.).

In another embodiment of the present disclosure, the hydrogel comprises about 3.0 wt % glycerin; about 87 wt % water; about 1.0 wt % denatured alcohol; about 6 wt % menthol (about 217 mg; about 26 mg/ml); and about 2.0 wt % full spectrum CBD or hemp oil (about 77 mg; about 9.4 mg./ml.).

In another embodiment of the present disclosure, the hydrogel comprises about 3.0 wt % glycerin; about 83 wt % water; about 1.0 wt % denatured alcohol; about 8 wt % menthol (about 386 mg; about 30 mg./ml.); and about 4.0 wt % full spectrum CBD or hemp oil (about 193 mg; about 15 mg./ml.).

All of the embodiments included here are with the proviso that the sum of ingredients in the exemplary compositions does not exceed 100%.

Embodiments of the present disclosure may be delivered for local or systemic administration to a body part of a person to be treated with the embodiment, for example, a body or skin surface by placing an embodiment of the present disclosure on a body part or skin surface thereof in active agent-transmitting relation thereto, the active agents being cannabinoid, for example, phytocannabinoid or full spectrum CDB or hemp oil, and menthol. Alternatively, an embodiment of the present disclosure may be incorporated into a delivery system, such as a unit dose delivery system (e.g. a "patch."). In manufacturing such systems, the hydrogel adhesive composition may be cast or extruded onto a backing layer or release liner and the surface from which the backing layer or release liner was removed can serve as the skin-contacting face of the system and act as an active agent reservoir. Alternatively, the hydrogel composition may be used as an active agent reservoir within the interior of such a system, with a conventional skin or other body part contact adhesive laminated thereto to affix the system to a body part or skin surface thereof. In such embodiments including a reservoir, the cannabinoid, for example, CBD or full spectrum CDB or hemp oil, could be in the reservoir and the menthol in the hydrogel housing the reservoir.

Other embodiments of the present disclosure include a method of relieving pain and/or inflammation by topically administering and placed topically to a body part (e.g., arm, leg, knee, torso, head, neck, foot as well as those parts that make-up them), of a mammal (e.g., a human patient or veterinary patient) in need of such treatment at least one of the compositions disclosed herein. Still other embodiments of the present disclosure include a method of relieving bodily pain (local and/or systemic) by topically administering to placed topically on a body part (e.g., arm, leg, knee, torso, head, neck, foot as well as those parts that make-up them), of a mammal (e.g., a human patient or veterinary patient) in need of such treatment at least one of the compositions disclosed herein. Still other embodiments of the present disclosure include a method of relieving pain and/or inflammation (local and/or systemic) by administering to a body part, for example, placed topically on an arm, leg, knee, torso, head, neck, foot as well as those parts that make-up them, of a mammal (e.g., a human patient or veterinary patient) in need of such treatment at least one of the compositions disclosed herein. Still other embodiments of the present disclosure include a method of relieving bodily pain and/or inflammation (local and/or systemic) by topically administering to placed topically on a body part (e.g., arm, leg, knee, torso, head, neck, foot as well as those parts that make-up them), of a mammal (e.g., a human patient or veterinary patient) in need of such treatment at least one of the compositions disclosed herein by placing the composition topically on a body part (e.g., arm, leg, knee, torso, head, neck, foot as well as those parts that make-up them).

For embodiments that are placed on a body part (e.g., patch embodiments), the dosing time can range from about 30 minutes to about 12 hours, about 30 minutes to about 8 hours (based on in vitro testing), 30 minutes to about 2 hours or about 30 minutes to about 1 hour. The greater the amount of glycerin, the longer the maximum the therapeutic dosing time The remainder can then be removed from the body part or skin surface thereof.

Another embodiment of the present disclosure relates to a composition containing particles which have a core containing an active agent or a salt thereof coated with a barrier layer. The barrier layer is formed from a coating liquid that contains a least one water insoluble barrier forming component selected from a group consisting of ethyl cellulose, copolymers of acrylic and methacrylic esters and natural or synthetic waxes, and a plasticizer.

The amount of the active agent administered may be dependent on the subject being treated, the severity of the disorder or condition, the rate of administration, the disposition of the compound and the discretion of the prescribing physician. However, an effective dosage is in the range of about 0.001 to about 100 mg. per kg body weight per day, preferably about 1 to about 35 mg./kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

Any standard manufacturing procedure known in the art may be used to manufacture the hydrous hydrogels of the present disclosure. For example, in a vessel (with or without mixing), at a temperature above 70° C., one could add in order, water, the biocompatible polymer (e.g., carrageenan), the polyalcohol (e.g., glycerin), a surfactant (e.g., polysorbate 80), the menthol and the CBD ingredient. The mixture from the vessel is cast or spread into a hydrogel film and passed through at refrigerated tunnel at about 30° C. to about 50° C. or colder. The colder the refrigerated tunnel, the less water that is evaporated or lost from the hydrogel film. The hydrogel film can then be cut or divided into various forms and sizes e.g., the embodiments of the present disclosure. After it is cut or divided, the hydrogel can be placed in its packaging and sprayed with the skin oil cleanser and/or cooling agent (e.g., denatured alcohol or isopropyl alcohol) to coat its exterior surface including surface areas shown in the figures of the present disclosure, immediately before sealing the package, for example, the package embodiment of the present disclosure.

The embodiments of the present disclosure (including hydrogel masses and patches) can be extruded directly onto a substrate such as a backing layer or release liner, and then pressed.

Systems for the topical or transdermal administration of an active agent may comprise: a reservoir containing a therapeutically effective amount of an active agent; an adhesive means for maintaining the system in active agent transmitting relationship to a body surface; and a backing layer as described above, wherein a disposable release liner covers the otherwise exposed surface, protecting such surface during storage and prior to such surface being applied topically (also as described above).

The compositions, patch or device of the present disclosure will contain a quantity of an active agent effective to provide the desired dosage or effect over a predetermined delivery period. The compositions, patch or device of the present disclosure include the hydrogel compositions as well as masses thereof including patches and other shapes that can be topically applied topically to a body part or portion thereof.

The compositions of the present disclosure may also include a rate-controlling membrane on the body surface side of the drug reservoir. The materials used to form such a membrane are selected to limit the flux of one or more components contained in the drug formulation, and the membrane may be either microporous or dense. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, polysiloxane-polycarbonate block copolymer and the like.

Figure 4A:
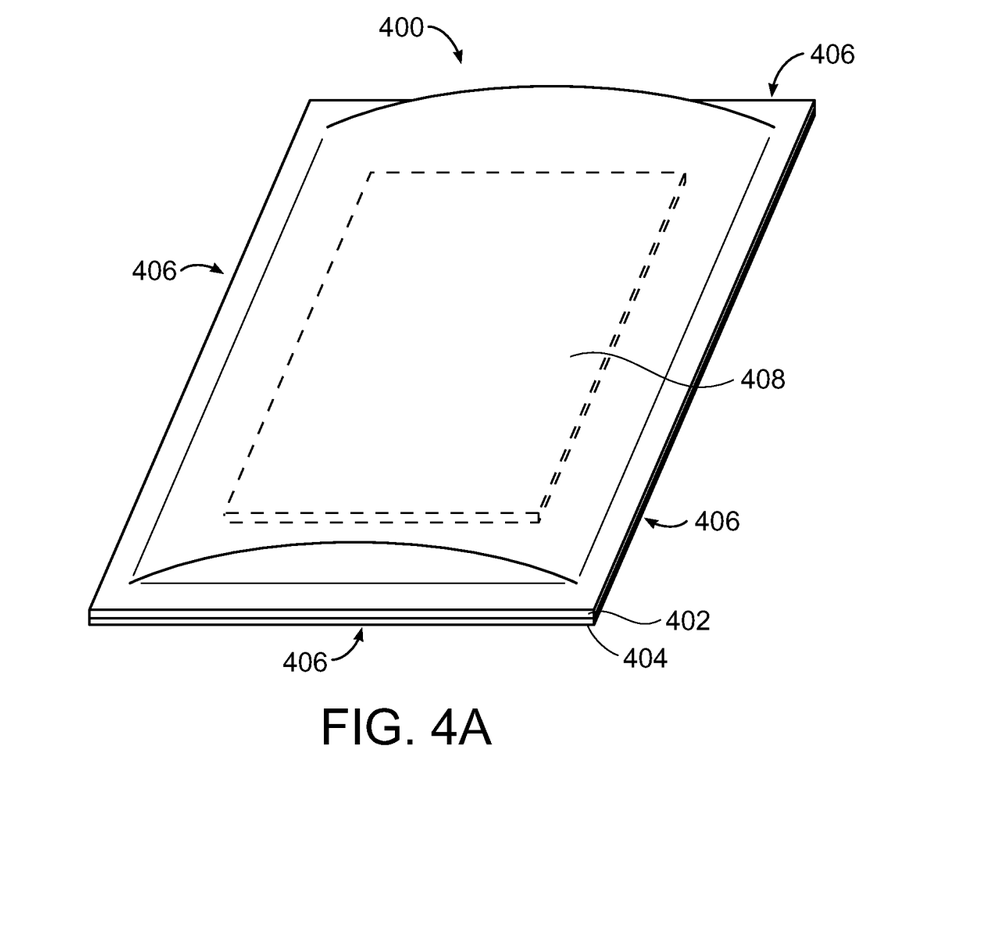
FIGS. 4A and 4B illustrate perspective and cross-sectional views of an exemplary packaging embodiment of the present disclosure.
Figure 4B:
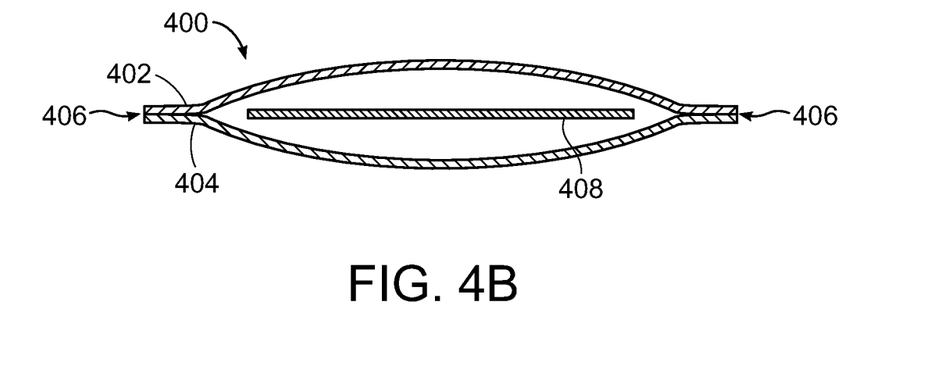

An example of such a kit is a sealed water-proof package containing an embodiment of the present disclosure. Another aspect of the present disclosure is a water-proof package designed to contain of the composition or patch embodiments of the present disclosure and to keep a substantial amount of the moisture (i.e., water) in the embodiment. One package embodiment is illustrated in FIGS. 4A and 4B and can include foil enclosure 400 with side sections 402 and 404 that are sealed together along a common peripheral edge 406. Inside the enclosure 400 is an internal void in which a patch 408 is positioned.

Example 1

Size of unit dose patch: 6.5 cm×4.2 cm (27.3 cm$^2$) with thickness from 0.0508 cm to 0.06604 cm. volume about 1.58 ml, total weight 762.62 mg. Ingredients: glycerin 3.0 wt % (21.8 mg.); water base material 91 wt % (661.22 mg.); denatured alcohol 1.0 wt % (7.27 mg.); menthol 5 wt % (36.33 mg; 23 mg./ml.); and full spectrum hemp oil 2.0 wt % (14.53 mg; 9.2 mg./ml.).

Example 2

Size of unit dose patch: 10 cm×14 cm (140 cm$^2$) with thickness from 0.0508 cm to 0.06604 cm. volume about 8.176 ml, total weight 3633 mg. Ingredients: glycerin 3.0 wt % (108 mg.); water base material 87.21 wt % (3168 mg.);

denatured alcohol 1.0 wt % (36 mg.); menthol 6 wt % (217 mg; 26.5 mg./ml.); and full spectrum hemp oil 2.10 wt % (77 mg; 9.4 mg./ml.).

Example 3

Size of unit dose patch: 12 cm×16 cm (192 cm²) with thickness from 0.0508 cm to 0.06604 cm. volume about 12.68 ml, total weight 4830 mg. Ingredients: glycerin 3.0 wt % (145 mg.); water base material 83.25 wt % (4021 mg.); denatured alcohol 1.0 wt % (48.3 mg.); menthol 8 wt % (386.4 mg; 30.4 mg./ml.); and full spectrum hemp oil 4.0 wt % (193.2 mg; 15.2 mg./ml.).

All publications, including but not limited to, issued patents, patent applications, and journal articles, cited in this application are each herein incorporated by reference in their entirety.

Thus, while there have been shown, described and pointed out, fundamental novel features of the present disclosure as applied to the exemplary embodiments thereof, it will be understood that various omissions and substitutions and changes in the form and details of devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

This written description uses examples as part of the disclosure, including the best mode, and also to enable any person skilled in the art to practice the disclosed implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

While there have been shown, described and pointed out, fundamental features of the present disclosure as applied to the exemplary embodiments thereof, it will be understood that various omissions and substitutions and changes in the form and details of compositions, devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

The invention claimed is:

1. A transdermal analgesic hydrogel device, comprising:
   a surface to be applied to the skin of a mammal, the surface having an area ranging in size from about 9 cm² to about 256 cm²;
   water in an amount of from about 70 wt % to about 95 wt %;
   a biocompatible polymer in an amount of from about 0.5 wt % to about 5 wt %;
   a polyalcohol in an amount of from about 1 wt % to about 5 wt %;
   at least one cannabinoid is in an amount of from about 0.1 wt % to about 10 wt %.; and
   a stabilized menthol composition comprising a preformed mixture of menthol and at least one menthol stabilizer compound including undecylenic acid methyl ester, undecylenic acid or a salt of undecylenic acid, wherein the therapeutic composition includes menthol in an amount of from about 1 wt % to about 10 wt % and the percentage amounts are all based on the total weight of the transdermal analgesic hydrogel device.

2. The transdermal analgesic hydrogel device of claim 1, wherein the biocompatible polymer is carageenan and the polyalcohol is glycerin.

3. The transdermal analgesic hydrogel device of claim 1, wherein the at least one cannabinoid includes full spectrum hemp oil.

4. The transdermal analgesic hydrogel device of claim 1, further including a skin oil cleanser in an amount of from about 0.1 wt % to about 2 wt %.

5. The transdermal analgesic hydrogel device of claim 4, wherein the skin oil cleanser includes denatured alcohol.

6. The transdermal analgesic hydrogel device of claim 4, wherein the at least one cannabinoid includes full spectrum hemp oil.

7. A transdermal analgesic hydrogel patch for topical application to the skin of a mammal, the transdermal analgesic hydrogel patch comprising:
   water in an amount of from about 70 wt % to about 95 wt %;
   carageenan in an amount of from about 0.5 wt % to about 5 wt %;
   glycerin in an amount of from about 1 wt % to about 5 wt %;
   full spectrum hemp oil in an amount of from about 0.1 wt % to about 10 wt %; and
   a stabilized menthol composition comprising a preformed mixture of menthol and at least one menthol stabilizer compound including undecylenic acid methyl ester, undecylenic acid or a salt of undecylenic acid, wherein the therapeutic composition includes menthol in an amount of from about 1 wt % to about 10 wt % and the percentage amounts are all based on the total weight of the transdermal analgesic hydrogel patch.

8. The transdermal analgesic hydrogel patch of claim 7, further including a skin oil cleanser in an amount of from about 0.1 wt % to about 2 wt %.

9. The transdermal analgesic hydrogel patch of claim 8, wherein the skin oil cleanser includes denatured alcohol.

10. The transdermal analgesic hydrogel patch of claim 7, wherein the full spectrum hemp oil includes less than 0.3% THC.

11. The transdermal analgesic hydrogel patch of claim 7, wherein the transdermal analgesic hydrogel patch is a unit dose formulation and includes full spectrum hemp oil in a unit dose amount of from about 2 mg. to about 195 mg. and menthol in a unit dose amount of from about 2 mg. to about 400 mg.

12. A method of treating pain or inflammation in a body part or portion thereof of a mammal using a transdermal hydrogel patch, the transdermal hydrogel patch including a unit dose formulation comprising:
- water in an amount of from about 70 wt % to about 95 wt %;
- carageenan in an amount of from about 0.5 wt % to about 5 wt %;
- glycerin in an amount of from about 1 wt % to about 5 wt %;
- full spectrum hemp oil in a unit dose amount of from about 2 mg. to about 195 mg; and a stabilized menthol composition comprising a pre-formed mixture of menthol and at least one menthol stabilizer compound including undecylenic acid methyl ester, undecylenic acid or a salt of undecylenic acid, wherein the therapeutic composition includes menthol in a unit dose amount of from about 2 mg. to about 400 mg. and the percentage amounts are all based on the total weight of the transdermal hydrogel patch, the method comprising topically administering the transdermal hydrogel patch to skin of the body part of the mammal.

13. The method of claim 12, wherein the full spectrum hemp oil is in an amount of from about 0.1 wt % to about 10 wt %.

14. The method of claim 12, wherein the menthol is in an amount of menthol in the transdermal hydrogel patch is from about 1 wt % to about 10 wt %.

15. The method of claim 12, wherein the transdermal hydrogel patch includes an adhesive laminated thereto and the method further includes affixing the transdermal hydrogel patch to the skin of the mammal.

16. The method of claim 12, wherein the transdermal hydrogel patch further includes a skin oil cleanser in an amount of from about 0.1 wt % to about 2 wt % and the method further comprising breaking up oil deposits on the skin surface to which the transdermal hydrogel patch is administered using the skin oil cleanser where the oil deposits interfere with the transdermal passage of the full spectrum hemp oil and menthol into tissue beneath the skin surface.

17. The method of claim 16, wherein the skin oil cleanser includes denatured alcohol.

18. The method of claim 12, further including topically administering the transdermal hydrogel patch for a minimum of about 30 minutes.

19. The method of claim 12, wherein the pain or inflammation being treated is at least one of local pain or inflammation and systemic pain or inflammation.

20. The method of claim 12, wherein the full spectrum hemp oil includes less than 0.3% THC.

* * * * *